(12) United States Patent
Chiang et al.

(10) Patent No.: US 7,615,024 B2
(45) Date of Patent: Nov. 10, 2009

(54) ELASTIC MATERIAL FOR COMPRESSION BRACES AND THE LIKE

(75) Inventors: Jackson Chiang, Taipei (TW); Jonathon Chuang, Brisbane (AU)

(73) Assignee: La Pointique International Ltd., Tukwila, WA (US)

( * ) Notice: Subject to any disclaimer, the term of this patent is extended or adjusted under 35 U.S.C. 154(b) by 314 days.

(21) Appl. No.: 11/608,223

(22) Filed: Dec. 7, 2006

(65) Prior Publication Data

US 2007/0077393 A1   Apr. 5, 2007

Related U.S. Application Data

(60) Division of application No. 10/845,470, filed on May 13, 2004, now abandoned, which is a continuation-in-part of application No. 10/355,652, filed on Jan. 29, 2003, now Pat. No. 7,090,651, which is a continuation-in-part of application No. 10/004,469, filed on Oct. 23, 2001, now Pat. No. 6,726,641, which is a continuation-in-part of application No. 09/846,332, filed on May 2, 2001, now Pat. No. 6,508,776.

(51) Int. Cl.
*A61F 5/00* (2006.01)

(52) U.S. Cl. .............................. 602/5; 602/6

(58) Field of Classification Search ............ 602/42–59, 602/5–7; 428/131
See application file for complete search history.

(56) References Cited

U.S. PATENT DOCUMENTS

| | | | |
|---|---|---|---|
| 2,570,182 A | 10/1951 | Daly | |
| 2,653,601 A | 9/1953 | Morrison | |
| 2,976,539 A | 3/1961 | Brown, Jr. | |
| 3,092,110 A | 6/1963 | Duensing | |
| 3,328,505 A | 6/1967 | Spencer | |
| 3,355,974 A | 12/1967 | Carmichael | |
| 3,451,232 A | 6/1969 | Belzidsky | |
| 3,600,717 A | 8/1971 | McKeehan | |
| 3,707,102 A | 12/1972 | Huppenthal | |
| 3,892,239 A | 7/1975 | Masso Remiro | |
| 3,990,440 A | 11/1976 | Gaylord, Jr. | |
| 3,991,424 A | 11/1976 | Prahl | |

(Continued)

FOREIGN PATENT DOCUMENTS

DE        3613488 A1    10/1987

(Continued)

*Primary Examiner*—Michael A. Brown
(74) *Attorney, Agent, or Firm*—Christensen O'Connor Johnson Kindness PLLC

(57) ABSTRACT

An elastic material is disclosed, including a breathable, closed cell foam panel. The elastic panel (310) includes recessed portions or channels (312) on at least one side, and apertures (314) therethrough, the apertures disposed in the channels (312). The channels may intersect to produce a network of flow paths for heat and sweat transfer, or may comprise nonintersecting channels that establish a directional flow path. In another embodiment, the channels define a plurality of protrusions, such as circular protrusions (332) or rectangular protrusions (342). The elastic panel is preferably formed by compressing a sheet of closed cell foam between a pair of oppositely disposed, heated plates (410, 420), wherein one of the plates includes a plurality of pins (422), and the other of the plates includes apertures (414) adapted to receive the pins. One or both of the plates includes protrusions (412) for forming the recessed portions or channels.

18 Claims, 14 Drawing Sheets

U.S. PATENT DOCUMENTS

| | | | |
|---|---|---|---|
| 3,998,220 A | 12/1976 | Cleer, Jr. | |
| 4,043,058 A | 8/1977 | Hollister | |
| 4,084,586 A | 4/1978 | Hettick | |
| 4,153,054 A | 5/1979 | Boone | |
| 4,272,850 A | 6/1981 | Rule | |
| 4,294,240 A | 10/1981 | Thill | |
| 4,470,411 A | 9/1984 | Hoyt, Jr. | |
| 4,474,573 A | 10/1984 | Detty | |
| 4,516,572 A | 5/1985 | Schlein | |
| 4,530,440 A | 7/1985 | Leong | |
| 4,541,426 A | 9/1985 | Webster | |
| 4,685,453 A | 8/1987 | Guignard | |
| 4,690,847 A | 9/1987 | Lassiter | |
| 4,710,415 A | 12/1987 | Slosberg | |
| 4,758,297 A * | 7/1988 | Calligarich | 156/251 |
| 4,832,010 A | 5/1989 | Lerman | |
| 5,014,689 A | 5/1991 | Meunchen | |
| 5,020,164 A | 6/1991 | Edwards | |
| 5,066,531 A * | 11/1991 | Legg et al. | 428/131 |
| 5,114,766 A | 5/1992 | Jacques | |
| 5,449,341 A | 9/1995 | Harris | |
| 5,474,524 A | 12/1995 | Carey | |
| 5,489,259 A | 2/1996 | Jacobs | |
| 5,643,185 A | 7/1997 | Watson | |
| 5,656,352 A | 8/1997 | Middleton | |
| 5,658,324 A | 8/1997 | Bailey, Sr. | |
| 5,735,807 A | 4/1998 | Cropper | |
| 5,834,093 A | 11/1998 | Challis | |
| 5,901,379 A | 5/1999 | Hirata | |
| 5,924,134 A | 7/1999 | Taylor | |
| 5,925,010 A | 7/1999 | Caprio, Jr. | |
| 5,948,707 A | 9/1999 | Crawley | |
| 6,093,468 A | 7/2000 | Toms | |
| 6,110,135 A | 8/2000 | Madow | |
| 6,129,695 A | 10/2000 | Peters | |
| 6,190,344 B1 | 2/2001 | Bobroff | |
| 6,503,855 B1 | 1/2003 | Menzies | |
| 6,508,776 B2 | 1/2003 | Chiang | |
| 6,520,926 B2 | 2/2003 | Hall | |
| 6,569,111 B2 | 5/2003 | Herzberg | |
| 6,617,485 B2 | 9/2003 | Herzberg | |
| 6,726,641 B2 | 4/2004 | Chiang | |
| 7,090,651 B2 | 8/2006 | Chiang | |
| 2002/0115950 A1 | 8/2002 | Domanski | |
| 2002/0146536 A1 | 10/2002 | Bard | |
| 2005/0010155 A1 | 1/2005 | Chiang | |

FOREIGN PATENT DOCUMENTS

| | | |
|---|---|---|
| DE | 4029685 A1 | 3/1992 |
| DE | 19812756 A1 | 10/1999 |
| EP | 0639361 A1 | 2/1995 |
| GB | 1094893 | 12/1967 |
| GB | 2299349 A | 10/1996 |
| GB | 2312643 A | 11/1997 |
| GB | 2375077 A | 11/2002 |
| JP | 01-141040 | 2/1998 |
| JP | 2003-033378 | 2/2003 |
| JP | 2004-098356 | 2/2004 |
| WO | 02065940 A2 | 8/2002 |

* cited by examiner

ELASTIC MATERIAL FOR COMPRESSION BRACES AND THE LIKE

CROSS-REFERENCES TO RELATED APPLICATIONS

This application is a division of U.S. patent application Ser. No. 10/845,470, filed May 13, 2004, which is a continuation-in-part of U.S. patent application Ser. No. 10/355,652, filed Jan. 29, 2003, which is a continuation-in-part of application Ser. No. 10/004,469, filed Oct. 23, 2001, which is a continuation-in-part of application Ser. No. 09/846,332, filed May 2, 2001, priority from the filing date of which is hereby claimed under 35 U.S.C. § 120.

FIELD OF THE INVENTION

This invention generally relates to breathable, elastic materials that are suitable for elastic compression braces, and to methods for forming such materials.

BACKGROUND OF THE INVENTION

Elastic compression braces are available in many forms. Commonly, such braces are composed of soft, elastic material so that when worn, they provide a certain amount of support for an injured joint. These types of braces, often purchased without a prescription or the need for skilled professional fitting, have been used for a number of years and have been commonly available as braces for the knee, ankle, thigh, wrist, elbow, chest, shoulder, or lower back. These resilient, pliable compression braces can be worn for sprains and strains, arthritis, tendonitis, bursitis, inflammation, to reduce discomfort during post-operative use, or to treat post-trauma discomfort.

The elastic compression braces are often made from synthetic rubber (e.g., polychloroprene). This particular material is desirable because of its combination of favorable properties useful in elastic compression braces. Polychloroprene rubber has good elasticity and a relatively high density, thereby providing good compression support and resistance to shear forces.

Polychloroprene rubber is a closed cell material and therefore does not dissipate heat very well during use. Its closed cell characteristics can be useful in retaining heat during use by reflecting emitted heat back into the bones and joints of the affected area. This localized concentration of heat can aid venous flow, help reduce edema, and make the soft tissues less susceptible to injury.

Although use of polychloroprene rubber in elastic compression braces can concentrate heat, the natural tendency of the closed cell material to prevent heat dissipation may cause problems for the user. When worn, the polychloroprene material braces are stretched to impart a compression load around the affected body area. This compression fit, combined with the high density of the material and the lack of air circulation and dissipation through the material, can result in heat discomfort and perspiration, and may lead to heat rashes. Prolonged use of such braces can cause the user to perspire constantly, resulting in discomfort, and often prompting the user to prematurely stop wearing the brace. In effect, the material itself dictates the length of time that the orthopedic brace can be worn. It is not uncommon for users to stop wearing such braces after about one to two hours. In an effort to provide better breathability, certain prior polychloroprene rubber braces have been manufactured with perforations or holes punched through the entire depth of the material. However, these braces may not retain sufficient structural integrity to serve as an effective compression brace for the wearer because neoprene material is removed from these braces.

In particular, prior art methods of punching or cutting holes into the braces can produce weaknesses in the material. The material is designed to be wrapped and/or stretched about a portion of the user, which results in elongation and deformation of the cut holes. Holes that are simply cut or punched into the material will cause local weakening of the material, and stretching may cause the material to tear in such regions.

Thus, there is a need for an elastic compression brace having sufficient structural strength and integrity to offer a sufficient level of compression support, while also dissipating heat during use to reduce or avoid undue perspiration and heat discomfort, especially during prolonged use.

SUMMARY OF THE INVENTION

The present invention is directed to an elastic panel or layer that may be used in a composite material-for example, for use in an orthopedic compression brace-and a method for making the elastic panel. The elastic panel includes aspects that improve the breathability of the panel-for example, to facilitate the rejection of heat and moisture in an orthopedic brace.

The elastic panel is formed from a sheet of closed cell foam, such as a neoprene sheet having a thickness between about 2.0 and 10.0 mm. One side of the elastic panel defines a recessed portion or channels that are formed by compressing the sheet of foam with oppositely disposed heated plates. A plurality of apertures is provided through the sheet of foam, the apertures being formed by penetrating the panel with heated pills. The apertures and channels are therefore formed without cutting any material away from the sheet of closed cell foam.

In an embodiment of the invention, the apertures are circular and have a diameter between about 0.5 and 3.0 mm. In another embodiment of the invention, the apertures are disposed in the channels.

A method of manufacturing a material suitable for use in a compression brace material, includes the steps of providing a sheet of closed cell foam material between an pair of heated plates, wherein one plate includes a plurality of spaced-apart pins and the other plate includes a plurality of spaced-apart apertures that are sized and spaced to engage the pins, and further wherein at least one of the plates includes a plurality of protrusions for forming channels in the sheet, urging the plate together to form apertures in the sheet, and maintaining a pressure between the first plate and the second plate for a period of time such that the protrusions impress a plurality of depressions on the sheet of closed cell foam material.

In an embodiment of the invention, at least one of the plates are heated to a temperature between about 145° C. and 160° C., and a pressure of about 50 kg/cm$^2$ is maintained for about 4-6 minutes to form the channels.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
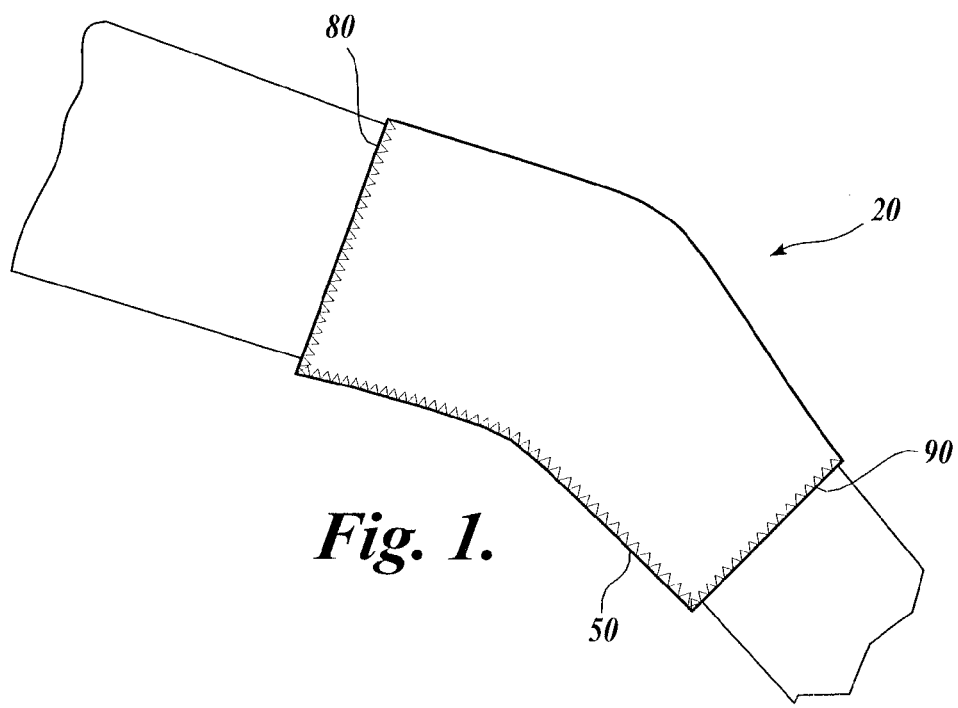
FIG. 1 is a side elevation view semi-schematically illustrating a knee brace made from an orthopedic material, according to principles of the present invention.
Figure 2:
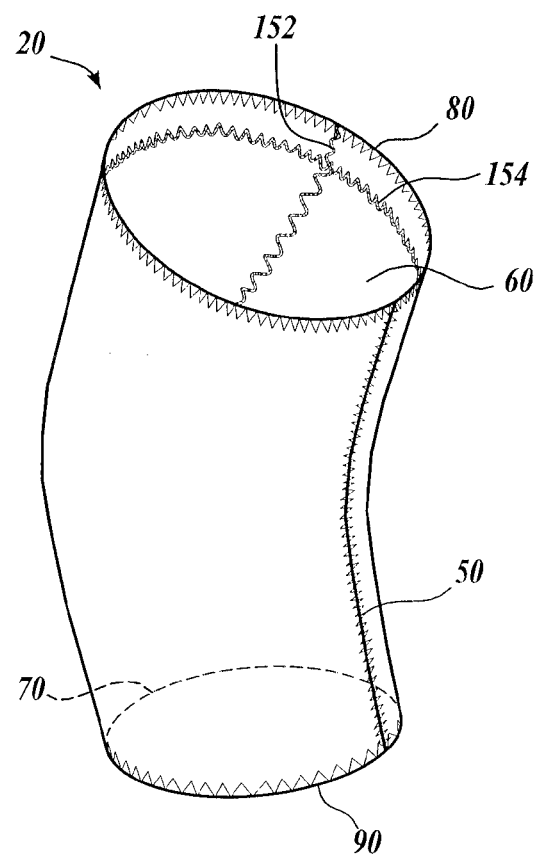
FIG. 2 is a semi-schematic perspective view of the knee brace shown in FIG. 1.
Figure 3:
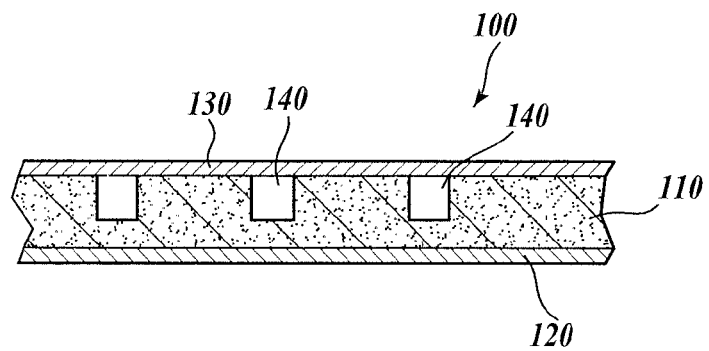
FIG. 3 is a cross-sectional view schematically illustrating components of a composite material of the present invention.
Figure 4:
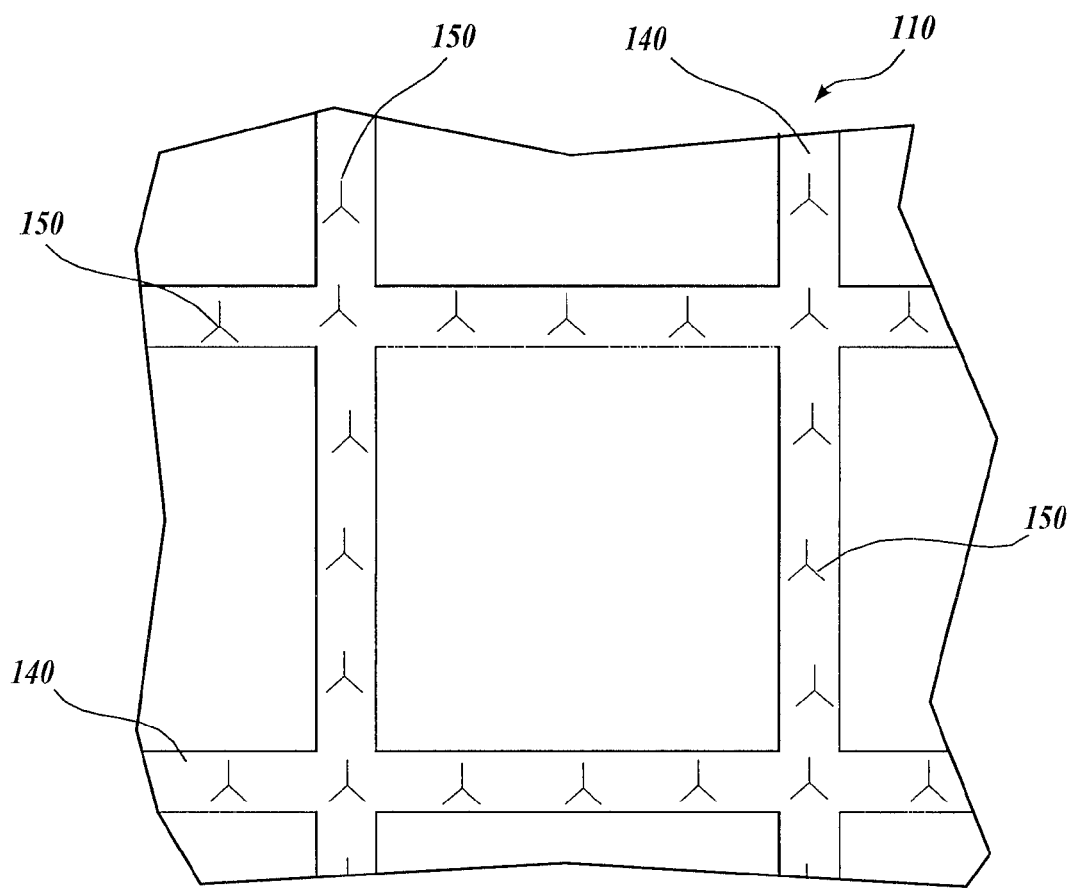
FIG. 4 is a frontal plan view illustrating a section of a punctured center layer of the composite material of the present invention.
Figure 5:
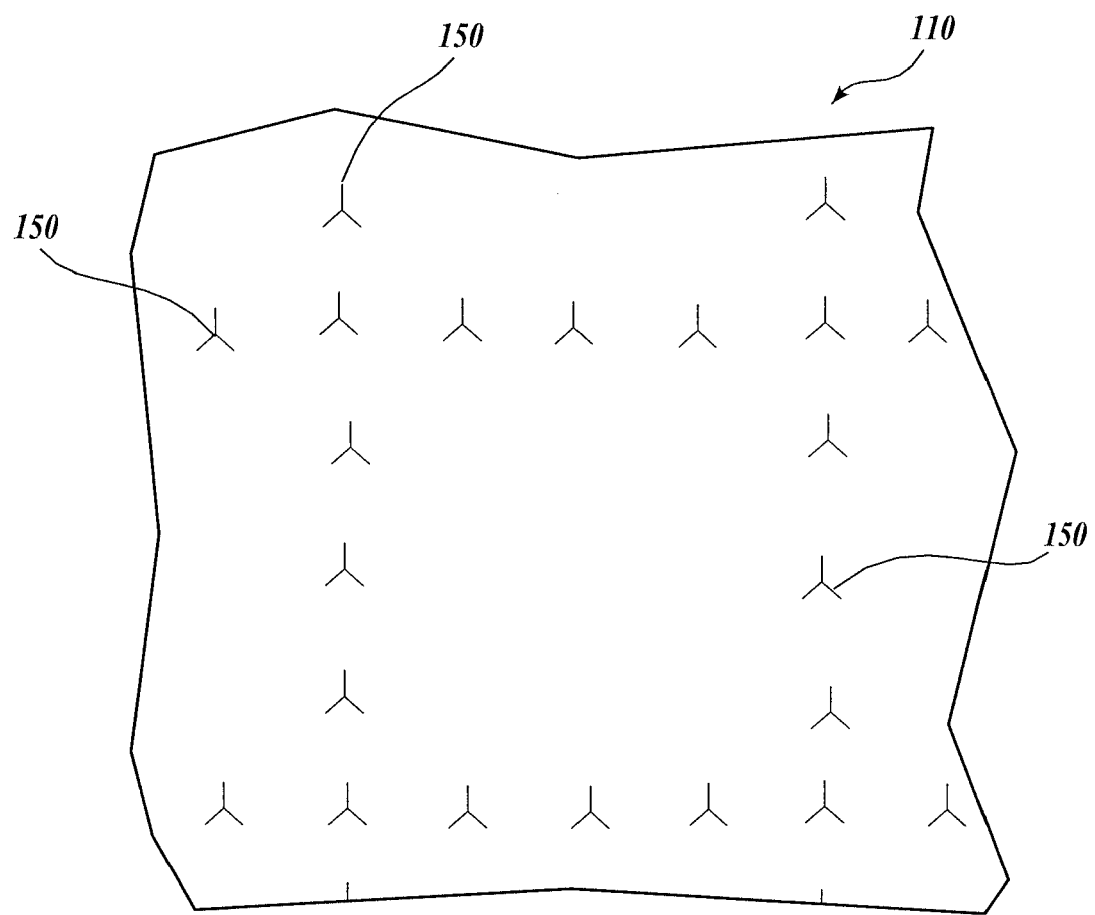
FIG. 5 is a back plan view illustrating a section of the punctured center layer shown in FIG. 4.

FIGS. 1 and 2 illustrate a knee brace 20 made from an orthopedic material according to principles of this invention. The orthopedic material is illustrated in FIGS. 3, 4, and 5. The knee brace is a soft orthopedic brace made from a flexible, resilient composite 100 shown in FIGS. 3, 4, and 5. The flat form composite material 100 is cut to shape and sewn or otherwise assembled to form a tubular knee brace 20, illustrated in FIGS. 1 and 2.

Referring to FIGS. 1 through 3, a piece of composite material 100 in flat sheet form is folded over on itself. The overlapping long edges on the opposite side of the fold are fastened by a long, upright seam 50. The material in the flat is cut in a shape so that when stitched along seam 50, as shown in FIGS. 1 and 2, an angular knee support of generally tubular form is produced having an open top 60 and an open bottom 70. Peripheral stitching 80 at the upper edge and similar peripheral stitching 90 at the bottom edge provide finished edges for the completed knee support.

The components that comprise the composite 100 are best understood by referring to FIGS. 3, 4, and 5. FIG. 3 shows a cross-sectional view illustrating the components of the composite 100 of the present invention. The composite material includes a flexible and foldable center elastic layer 110, an inner fabric layer 130, and an outer fabric layer 120. The center elastic layer 110 is preferably from a closed cell foam material in sheet configuration. One preferred elastic closed cell material is polychloroprene rubber, commonly known as neoprene rubber. Preferred neoprene materials are articles of commerce. Another suitable material for center layer 110 is styrene butadiene rubber (SBR). These materials are available in a wide density range, so it is not difficult to find material of a desired density that provides the desired level of support and provides good orthopedic compression during use. Ideally, such material for the purposes of the present invention is from 1.5 mm to 8.0 mm thick. However, other thicknesses may be used. Also, other elastic closed cell materials may be used to form layer 110.

The center elastic layer 110 has formed therein on one side thereof a plurality of intersecting grooves or channels 140. In non-limiting example, one embodiment of the present invention shows the pattern of intersecting channels 140 is formed by placing neoprene sheet material down on a metal mesh and then placing a weighted heat source on top of the flat sheet material. The pressure and heat cause the mesh to depress into the sheet material to permanently take the shape of the metal mesh on the underside where the grid pattern of the metal mesh is pressing into the sheet material. In addition or alternatively, the mesh may be preheated.

In another embodiment of the present invention, a pattern of intersecting channels 140 is formed on both surfaces of the sheet material. This can be accomplished in one manner by sandwiching the center layer 110 between top and bottom metal grids and heat pressing both grids against center layer 110, causing both grids to depress into the surfaces of the sheet material. The grid pattern may be identical on both sides of the center layer 110, or may be of different configurations.

In the embodiment shown in FIGS. 3 and 4, the plurality of intersecting channels 140 formed in center elastic layer 110 define a generally rectangular or square-shaped pattern or grid. It is to be appreciated that the pattern can be of any other shape, e.g., diamonds, triangles, ovals, circles, etc., as long as the channels 140 intersect each other so as to provide a continuous or interconnected passageway across the sheet material and along the length of the material.

The center elastic layer 110 may be punctured to form a multiplicity of punctures or cuts 150 through the layer. Cuts 150 are not shown in FIG. 3 for simplicity but are shown in FIGS. 4 and 5. FIG. 4 is a frontal plan view showing a section of punctured center layer 110. FIG. 5 is a back plan view showing a section of the punctured center layer 110 shown in FIG. 4. The multiplicity of cuts 150 are dispersed across the surface of center elastic layer 110 and extend through the entire depth of the layer so that fluids, including perspiration and air, can pass through the cuts 150 from one side of the layer to the other, especially when the layer is stretched.

In one embodiment of the present invention, cuts 150 are located only in registry with the channel portions 140. In another embodiment, cuts 150 are located not only within the channels 140, but also in the ungrooved/channeled portion of elastic layer 110. The cuts 150 may be located only at the intersections of the channels 140, or a multiplicity of cuts 150 may be of uniform pattern and spaced apart uniformly about the center elastic layer 110. Ideally, the multiplicity of cuts 150 should not be so large or the cuts spaced so close together that the overall structural integrity of the neoprene material is reduced beyond the ability of the material to provide sufficient orthopedic compression support during use.

The multiplicity of cuts 150 may define a cut pattern. FIGS. 4 and 5 show a cut pattern having three "legs" that radiate from a common point. It is to be appreciated, however, that the cut pattern may be any shape, such as a straight line, a curved line, a cross, or a five-legged pattern, without departing from the scope of the present invention. It is to be further appreciated that preferably the puncture does not actually remove any significant material, if any, from center elastic layer 110 or channels 140; rather, the puncture simply extends through the channels. Thus, the puncture does not form a hole or passage through the neoprene material unless the material is stretched.

The pattern for the multiplicity of cuts 150 may be formed in center elastic layer 110 by a number of methods. One such method of forming a cut pattern in the neoprene material is by a roller having a cylindrical outer surface with projecting punches in the desired cut pattern so that rolling the roller over the flat surface of the neoprene material punches out cuts in the desired pattern.

Referring back to FIG. 3, composite material 100 also includes a soft, flexible, resilient, porous inner fabric layer 130. Inner layer 130 may be a knitted flexible and foldable, stretchable cloth fabric material that is porous to air and water because of the pores inherently formed by the knitted fabric. Composite material 100 also includes a flexible and elastic, porous outer fabric layer 120, which also may be made from a stretchable knitted fabric of the same or different type from layer 130. The inner and outer fabric layers 130 and 120, respectively, may also be made from other stretchable knitted fabrics including nylon, Dacron® or other synthetic fibers.

After the center elastic layer 110 is altered with a plurality of intersecting channels 140 on one side thereof and punctured with a cut pattern 150, inner fabric layer 130 is bonded to the grooved face of center layer 110, while outer fabric layer 120 is bonded to the non-grooved face of center layer 110. Inner fabric layer 130 may be adhered to the center layer 110 using an adhesive technique that prevents the glue or other adhesive from being placed in channels 140. As such, the adhesive does not close or obstruct channels 140. Outer fabric layer 120 is also glued or otherwise adhered or bonded to center layer 110. The adhesive bonds the entire contacting surface areas of the center layer 110 and the adjoining number and outer fabric layers 130 and 120, respectively. It is to be noted that the adhesive does not disrupt the porosity of the center layer 110 and the inner or outer layers 130 and 120.

Returning to FIGS. 1 and 2, knee brace 20 is intended to be worn with the grooved/channeled side facing the body of the wearer. This provides the advantageous result of retaining heat against the body while allowing knee brace 20 to be breathable. Furthermore, because knee brace 20 is made from the composite material, it has sufficient porosity that internal heat build-up during use is essentially avoided. Knee brace 20 also provides good compression around a body part supported by knee brace 20 in its stretched condition. The elastic center layer retains substantially all of its ability to apply a compression load on the body portion being braced because material is not actually removed from the neoprene center layer, as in some conventional braces. Additionally, knee brace 20 is of sufficient density due to the neoprene, SBR, or other selected material to provide the compression necessary to serve as a useful knee brace. The inner and outer layers 130 and 120 also provide additional compressive strength to knee brace 20.

Knee brace 20 also provides good breathability. When knee brace 20 is in use, it stretches in a bidirectional manner, thereby creating a pumping action to allow air to flow through the channels 140 of knee brace 20. This carries body sweat through channels 140 and out the ends of knee brace 20. Knee brace 20 also allows fresh, cool air to pass inwardly through knee brace 20 to reach the body. Correspondingly, a certain amount of heat is able to pass from inside knee brace 20 to the outside through the plurality of cuts 150, which open up as the brace is stretched during use.

In accordance with a further aspect of the present invention, silicone 152, in the form of a gel or beads, may be applied along the inside of knee brace 20 lengthwise of the brace, perhaps on opposite sides of the brace. Additionally or alternatively, the silicone beads 154 may be placed circumferentially around the inside of the brace, perhaps near the ends of the brace. The silicone may be applied in a stripe of some width, in a narrow line or band, or in other patterns. Moreover, the stripe or line of silicone may be straight or curved. This silicone material causes the brace to stay in place on the body due to the friction between the silicone and the body. The silicone does not, however, cause discomfort or undue rubbing against the body.

In one embodiment, the silicone may be applied to the interior of knee brace 20 after the brace has been fully constructed. In another embodiment, the silicone is applied to the inside of inner fabric layer 130 of knee brace 20 and then the inner layer 130 is applied to the inside surface of center layer 110. As those skilled in the art will appreciate, other materials, in addition to silicone, may be employed to cause the brace to stay in place on the body, without departing from the scope of the present invention.

Figure 6:
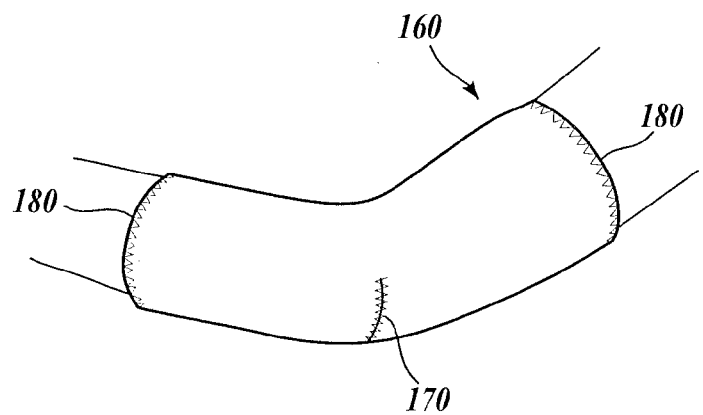
FIG. 6 is a perspective view illustrating an elbow brace made from the composite material of the present invention.
Figure 7:
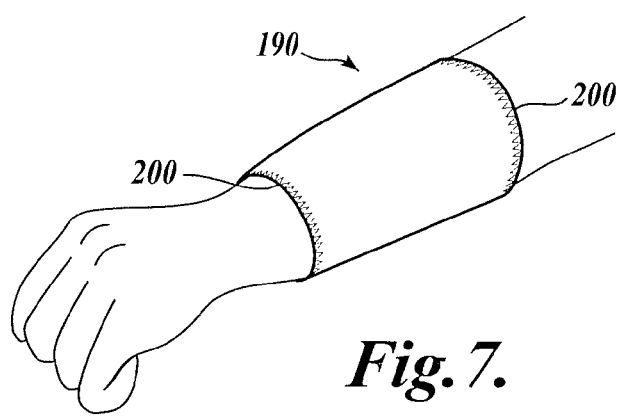
FIG. 7 is a perspective view illustrating a wrist brace made from the composite material of the present invention.
Figure 8:
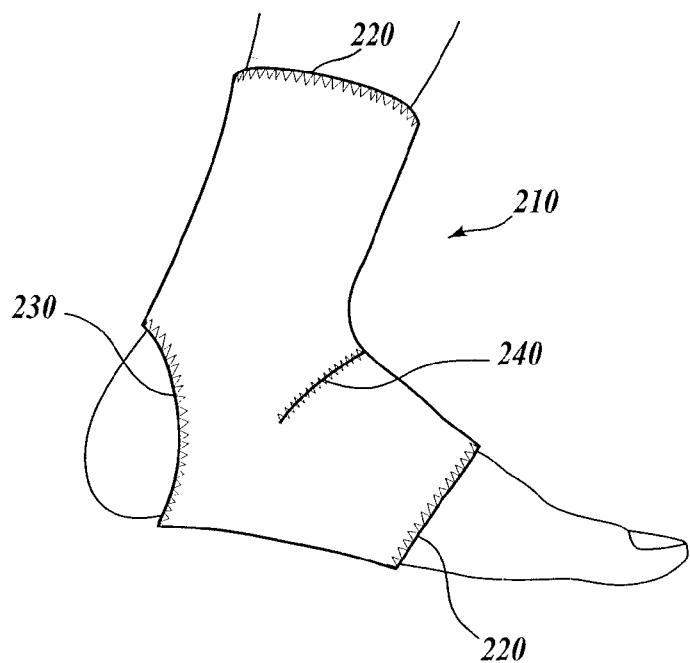
FIG. 8 is a side view illustrating an ankle brace made from the composite material of the present invention.

FIGS. 6-8 illustrate further uses of the composite material 100 in compression braces. FIG. 6 shows an elbow brace 160 in which composite material 100 is folded and seamed along its length. The brace may have an intermediate seam 170 to form a generally L-shaped tubular elastomeric brace. The top and bottom edges of the tubular brace have stitched peripheral seams 180 for edge reinforcement. FIG. 7 illustrates a wrist brace 190 made from the composite material 100, in which the material is folded and seamed lengthwise to form a generally straight tubular brace having peripheral stitching 200 at its opposite ends for edge reinforcement. FIG. 8 illustrates an ankle brace 210 made from composite material 100. The ankle brace 210 is formed as a generally L-shaped tubular brace with peripheral stitching 220 at its opposite ends, peripheral stitching 230 around an edge portion of the brace that fits around the heel of the user. The brace may include intermediate stitching 240 fastening adjoining intermediate edges of the L-shaped ankle support.

These compression braces can be used to provide required levels of anatomical compression support while improving ventilation to the supported area to reduce the discomfort caused by perspiration and over-heating. The improved composite material of this invention thus improves the anatomical support provided by compression braces, because the user is able to wear the brace for extended periods rather than having to remove the brace prematurely because of heat discomfort.

Figure 9:
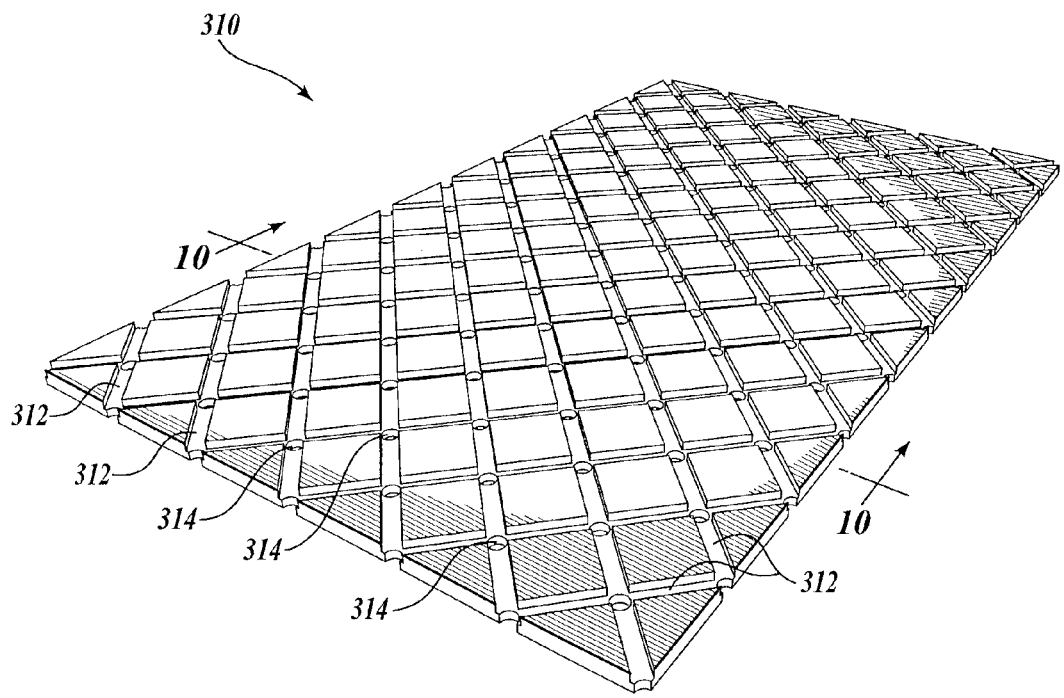
FIG. 9 is a perspective view of another embodiment of an elastic layer, having a plurality of intersecting channels and apertures therethrough.
Figure 10:
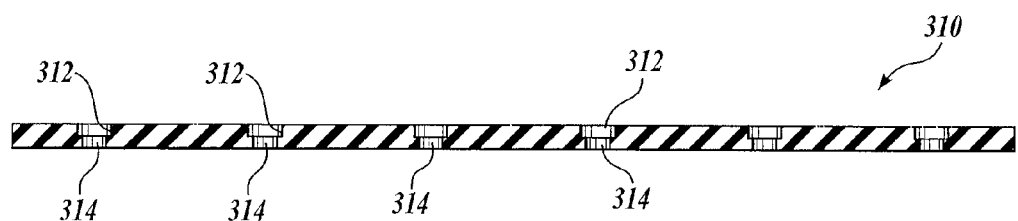
FIG. 10 is a cross-sectional side view of the elastic layer shown in FIGS. 9.

An alternative embodiment of an elastic layer 310 is shown in FIGS. 9 and 10, wherein FIG. 9 shows a perspective view of the elastic layer 310 and FIG. 10 shows a cross-sectional view of the elastic layer 310 through section 10-10. The elastic layer 310 includes a plurality of channels 312 arranged in an intersecting pattern and a number of small, generally circular apertures 314 through the elastic layer 310. The apertures 314 of this preferred embodiment are positioned at intersections of the channels 312, although it is contemplated that not every intersection need have an aperture 314, and/or additional apertures may be provided in the channels 312 at intermediate locations.

The combination of intersecting channels 312 and open apertures 314 provides a network for air and moisture to flow from one side of the elastic layer 310 to the other, while still retaining sufficient elasticity in the elastic layer 310 to produce the desired compressive force. As discussed in more detail below, the open apertures 314 may be formed using heated pins that penetrate the material to form the apertures 314, such that the material is partially softened or melted, resulting in a reinforcement of the material about the apertures 314. The center elastic layer 310 is preferably made from a sheet of a closed cell polymeric foam material such as neoprene, as discussed in more detail below.

It will be appreciated that the elastic layer 310 may be combined with outer and inner fabric layers such as are identified as 120 and 130, respectively, in FIG. 3. It will be appreciated that the circular apertures 314 differ from the cuts 150 of the embodiment shown in FIG. 4, in that the apertures 314 are "open," even when the elastic layer 310 is not stretched. It is also contemplated that the apertures 314 may be other than circular in shape, while retaining the aspect of being always open.

In use, the elastic layer 310, which may be combined in a composite material as discussed above, would normally be oriented with the open portion of the channels 312 facing inwardly, toward the user, thereby promoting lateral air and moisture flow towards the apertures 314 next to the user's skin, and thereby promoting the expulsion of moisture and heat away from the user.

Figure 11:
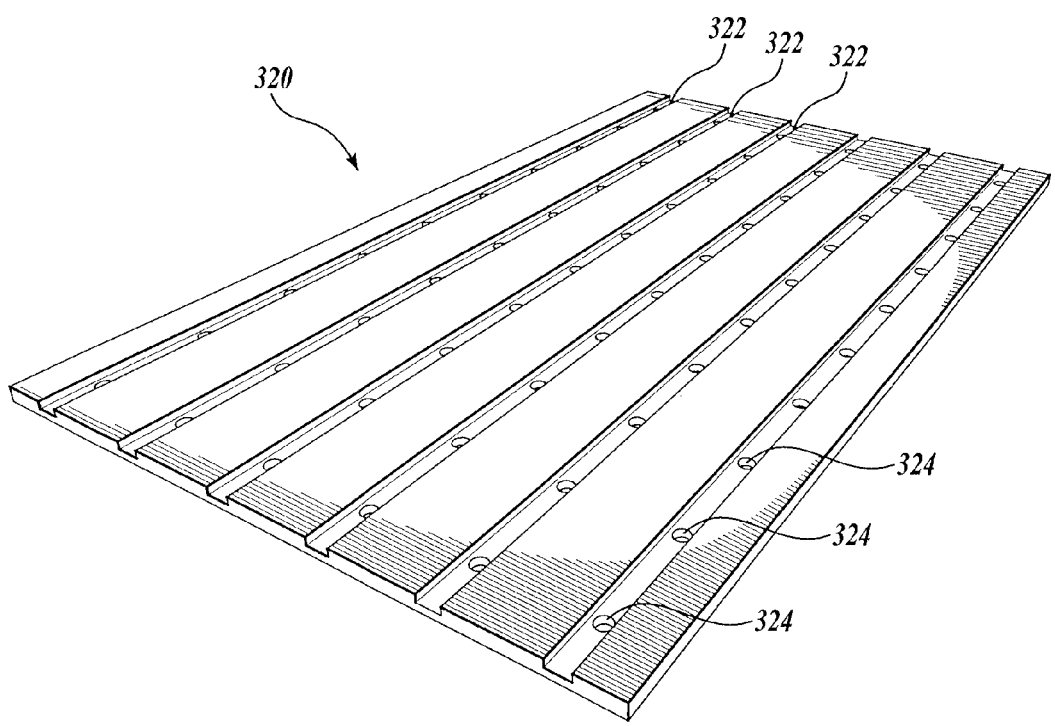
FIG. 11 is a perspective view of another embodiment of an elastic layer, having a plurality of nonintersecting channels and apertures therethrough.
Figure 12:
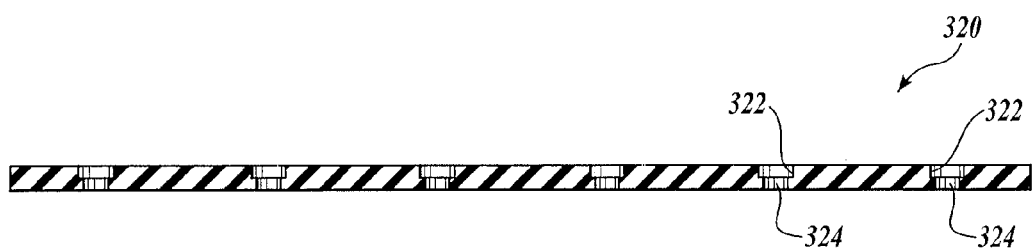
FIG. 12 is a cross-sectional side view of the elastic layer shown in FIG. 11.

FIGS. 11 and 12 show a perspective view and a cross-sectional view, respectively, of another alternative embodiment of a elastic layer 320, wherein the elongate channels 322 do not intersect with each other, but rather are oriented longitudinally along the elastic layer 320. A plurality of apertures 324 extends through the elastic layer 320, the apertures 324 being disposed generally within the elongate channels 322. The use of parallel, longitudinal channels 322 produce an anisotropic flexibility in the elastic layer 320 that results in less elasticity (greater stiffness) in the longitudinal direction, relative to the elasticity in the transverse direction. The parallel channels 322 also will permit a more directional flow of heat and moisture, whereby the material may be optimized for a particular application. Using this material, the designer may orient the elastic layer 320 such that the channels 322 are directed along a preferred direction—for example, to take advantage of the geometry or natural circulatory pattern for the particular body part that the elastic layer 320 is intended to envelop.

Figure 13A:
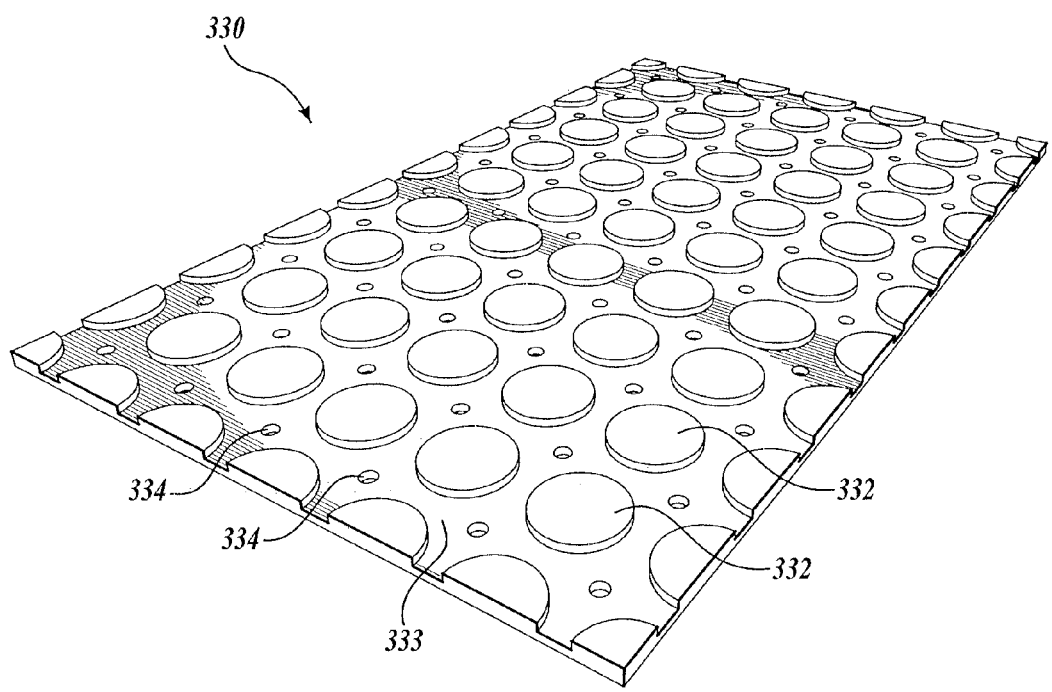
FIGS. 13A, 13B, and 13C are perspective views of additional embodiments of elastic layers having recessed areas, protruding areas, and apertures, according to the present invention.
Figure 13B:
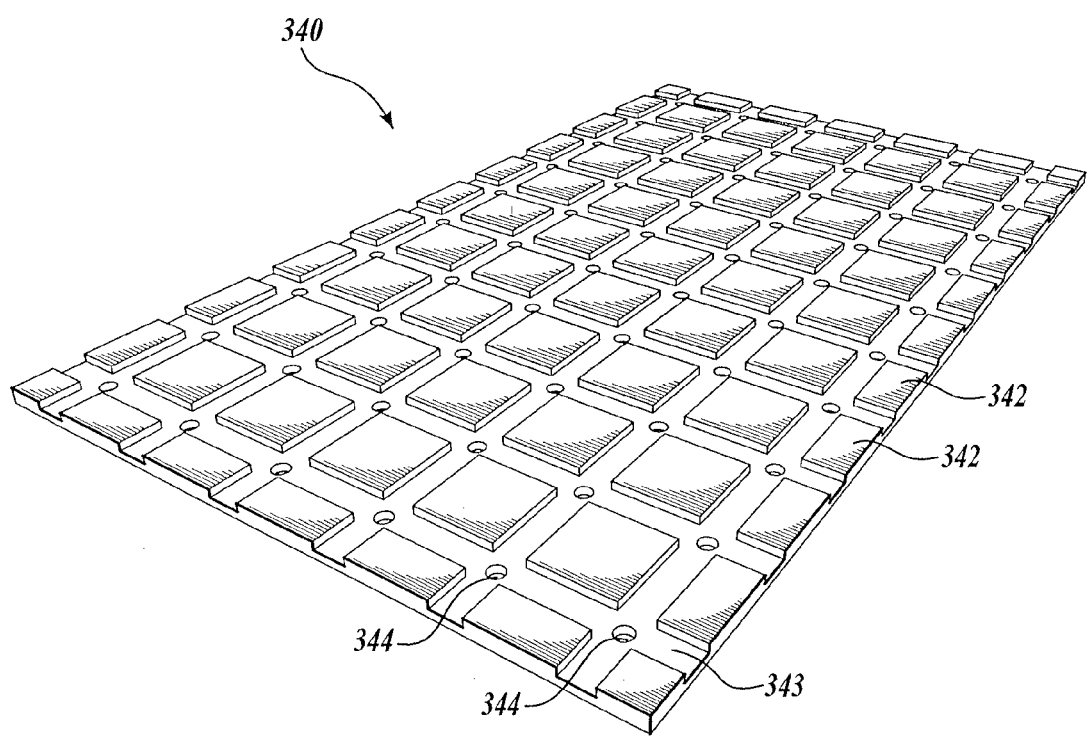
Figure 13C:
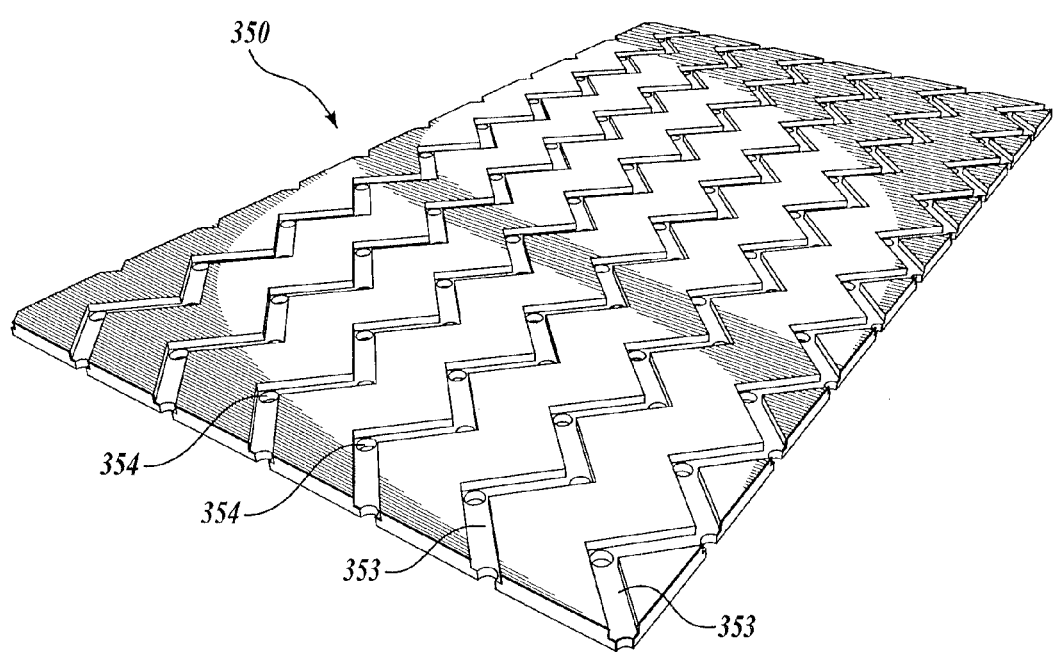

FIGS. 13A, 13B, and 13C show several exemplary alternative embodiments of elastic layers 330, 340, 350 that are contemplated by the present invention. In particular, FIG. 13A shows an elastic layer 330 having a plurality of circular protrusions 332 arranged in a regular pattern on the elastic layer. The recessed portion 333 of the elastic layer 330 between the protrusions 332 includes a plurality of apertures 334 that extend through the elastic layer 330. Similarly, FIG. 13B shows an elastic layer 340 having a plurality of square or rectangular protrusions 342 arranged in a regular pattern on the elastic layer. The recessed portion 343 of the elastic layer 340 between the protrusions 342 includes a plurality of apertures 344 that extend through the elastic layer 340. FIG. 13C shows an elastic layer 350 having a plurality of wavy channels 353 that extend longitudinally along the elastic layer 350, wherein a plurality of apertures 354 is disposed in the wavy channels 353. It will be readily apparent that other patterns for the channels (or protrusions) are possible.

Figure 14:
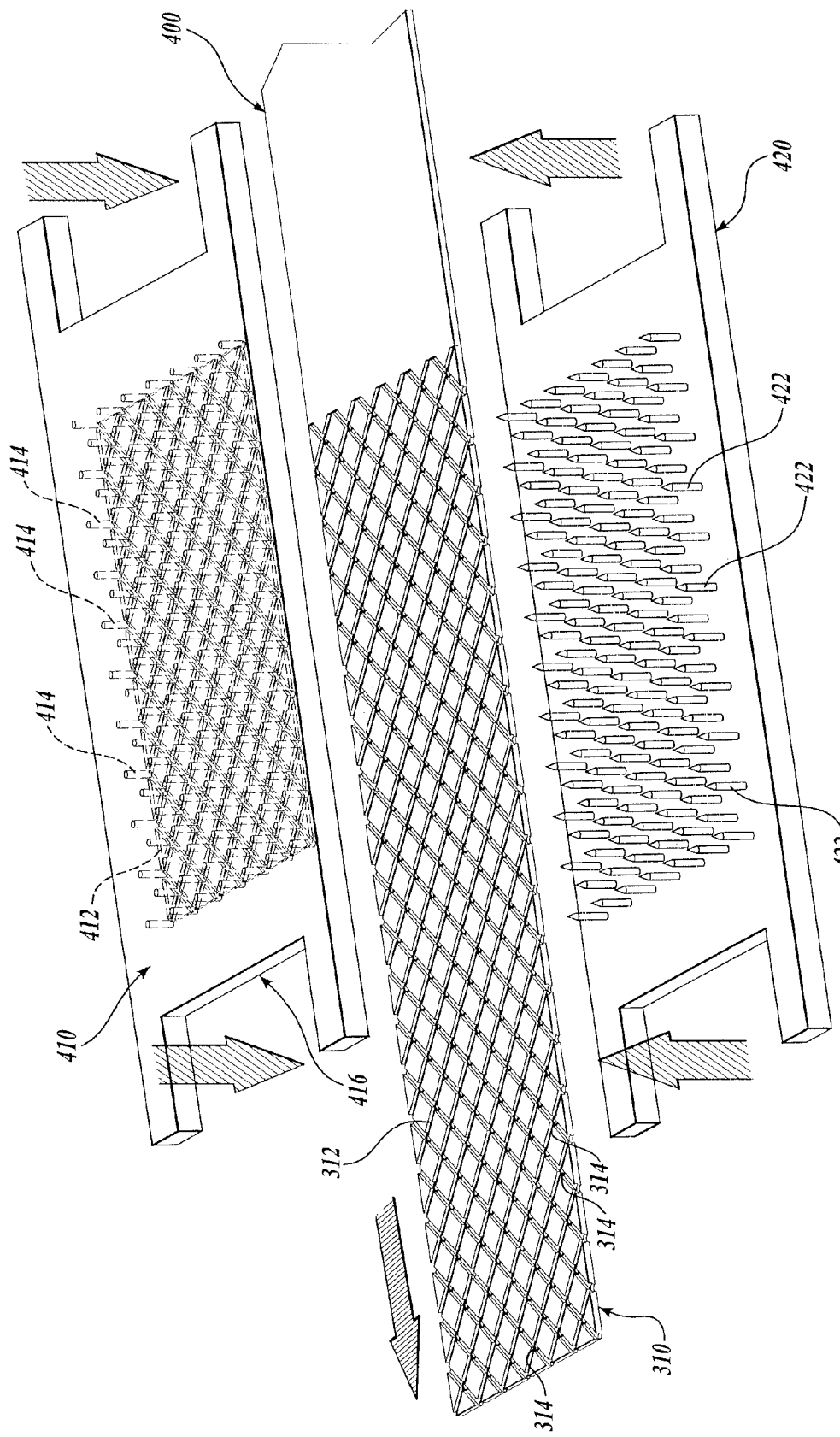
FIG. 14 is a perspective view illustrating a method for making the elastic layers utilizing a set of opposed plates.
Figure 15:
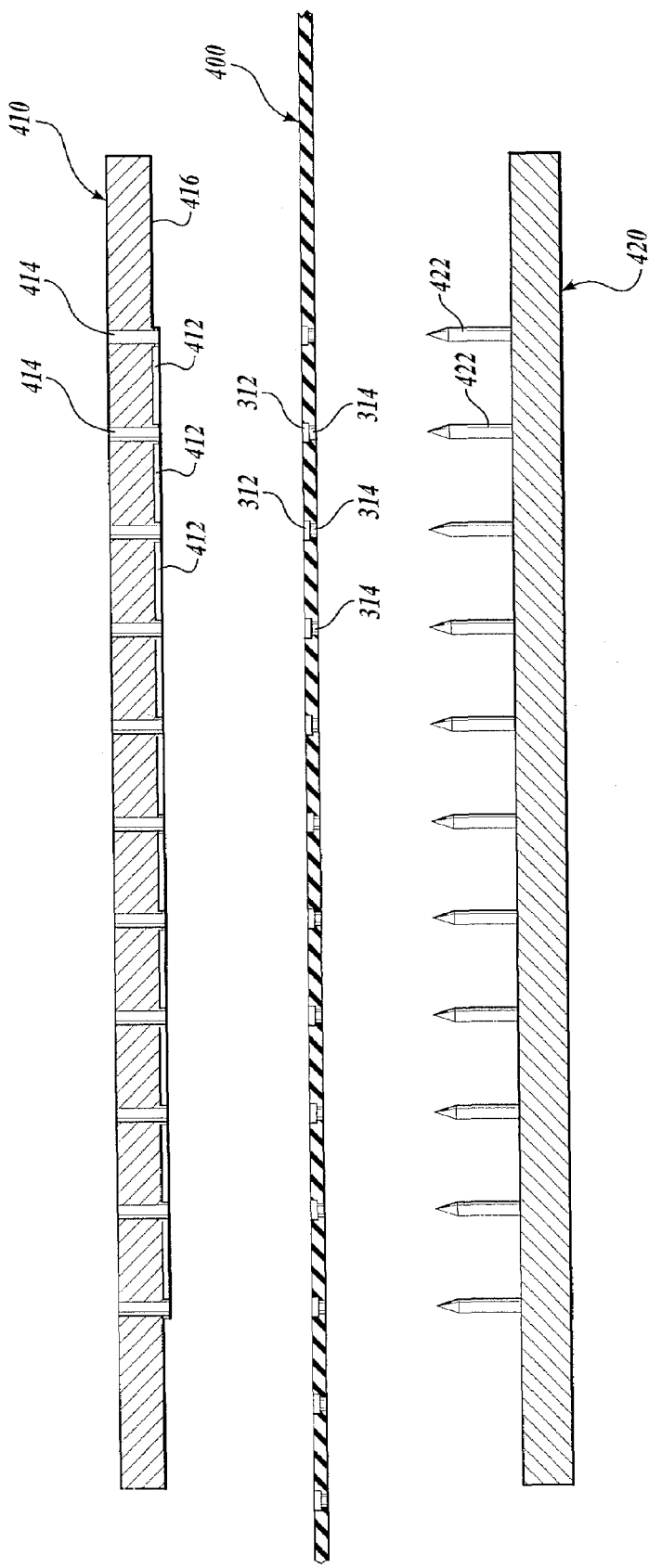
FIG. 15 is a cross-sectional side view of the opposed plates shown in FIG. 14.

Referring now to FIGS. 14 and 15, an exemplary method for producing the elastic material will be described. Although the disclosed method is shown for the elastic layer 310 shown in FIGS. 10 and 11, it will be appreciated that the method may be used to produce any of the elastic layers shown in FIGS. 9-13C.

As shown in FIG. 14 and the cross-sectional side view of FIG. 15, the elastic layer 310 may be formed utilizing an upper plate 410 and a lower plate 420. In a preferred embodiment, a sheet 400 of a closed cell polymeric material, such as neoprene, is disposed between the upper plate 410 and the lower plate 420. The sheet 400 is preferably between about 2.0 mm and 10.0 mm in thickness. The upper plate 410 includes a plurality of apertures 414 that extend at least partially through the upper plate 410 from the lower surface 416. The lower plate 420 includes a corresponding plurality of upwardly extending pins 422 that are sized and positioned to slidably engage the plurality of apertures 414 when the upper and lower plates 410, 420 are urged together. The pins 422 preferably have a diameter of between about 0.5 mm and 3.0 mm, and the apertures corresponding apertures 414 are slightly larger in diameter than the pins 422.

The upper plate 410 also includes a pattern of elongate protrusions 412 on its lower surface 416 that are adapted to form the desired pattern of indentations or channels 312 on the polymeric sheet 400. In a preferred embodiment, the pins 422 (and apertures 414) are spaced about 10.0 mm-15.0 mm apart, and the elongate protrusions 412 are two sets of intersecting, parallel linear protrusions, each set of linear protrusions having a line spacing of 10.0 mm-15.0 mm. The elongate protrusions 412 are preferably about 1.0 mm-2.0 mm high.

The plates 410, 420 are heated and the polymeric sheet 400 is disposed therebetween. The upper and lower plates 410, 420 are then moved or urged together, such that the heated pins 422 on the lower plate 420 puncture the sheet 400 to produce apertures 314 therein, and slidably engage the apertures 414 on the upper plate 410. The heated plates 410, 420 are held together for a period of time to form the pattern of channels 312 in the sheet 400. In a preferred mode the upper and lower plates 410, 420 are heated to a temperature of between about 145° C. and 160° C., and the plates 410, 420 are held together for about 4-6 minutes, with a biasing pressure of approximately 50 kg/cm$^2$.

As indicated by the arrows in FIG. 14, the upper and lower plates 410, 420 are pushed together to generate the pattern of apertures channels 312 and apertures 314 in the sheet 400. After the desired time, the plates 410, 420 are separated, to permit the sheet 400 to be removed and replaced, or shifted longitudinally to repeat the process on another portion of the sheet 400. It will be readily apparent the particular orientation of the upper and lower plates 410, 420 is not important, and that the method may alternatively be accomplished with the plates switched or the entire assembly rotated an arbitrary amount.

The present method provides several advantages. The plurality of apertures 314 and the pattern of channels 312 are formed simultaneously, in a single step, simplifying the manufacturing process. Also, utilizing heated plates 410, 420 and pins 422 to form the apertures 314 and channels 312 result in a relatively thick and/or strengthened region about the perimeter of the apertures 314 and channels 312, reducing the likelihood of tears in the material and helping to maintain the overall strength of the material. It will be readily appreciated that the method does not require cutting away any material from the sheet 400.

Figure 16:
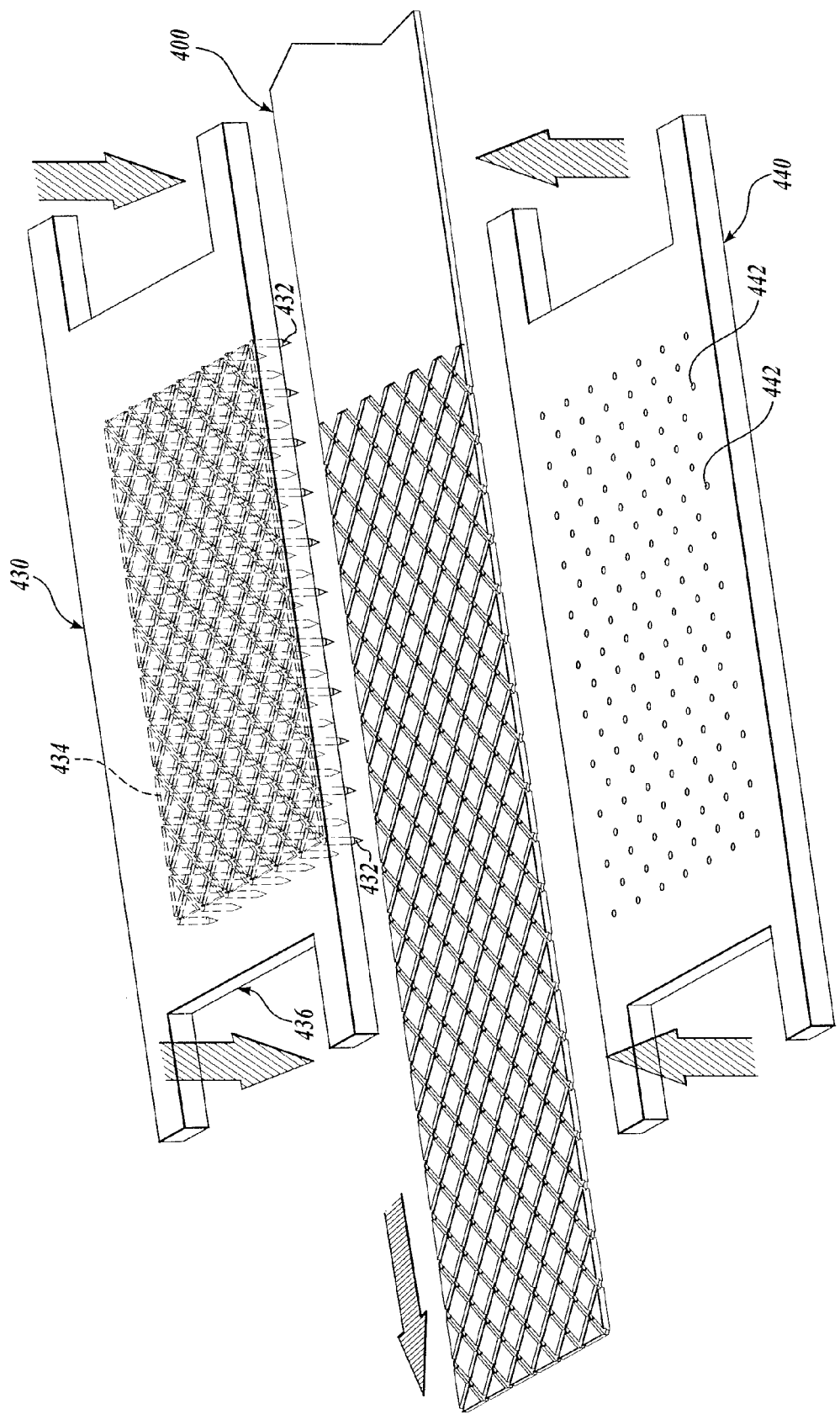
FIG. 16 is a perspective view illustrating another method for making the elastic layers, with a different set of opposed plates.
Figure 17:
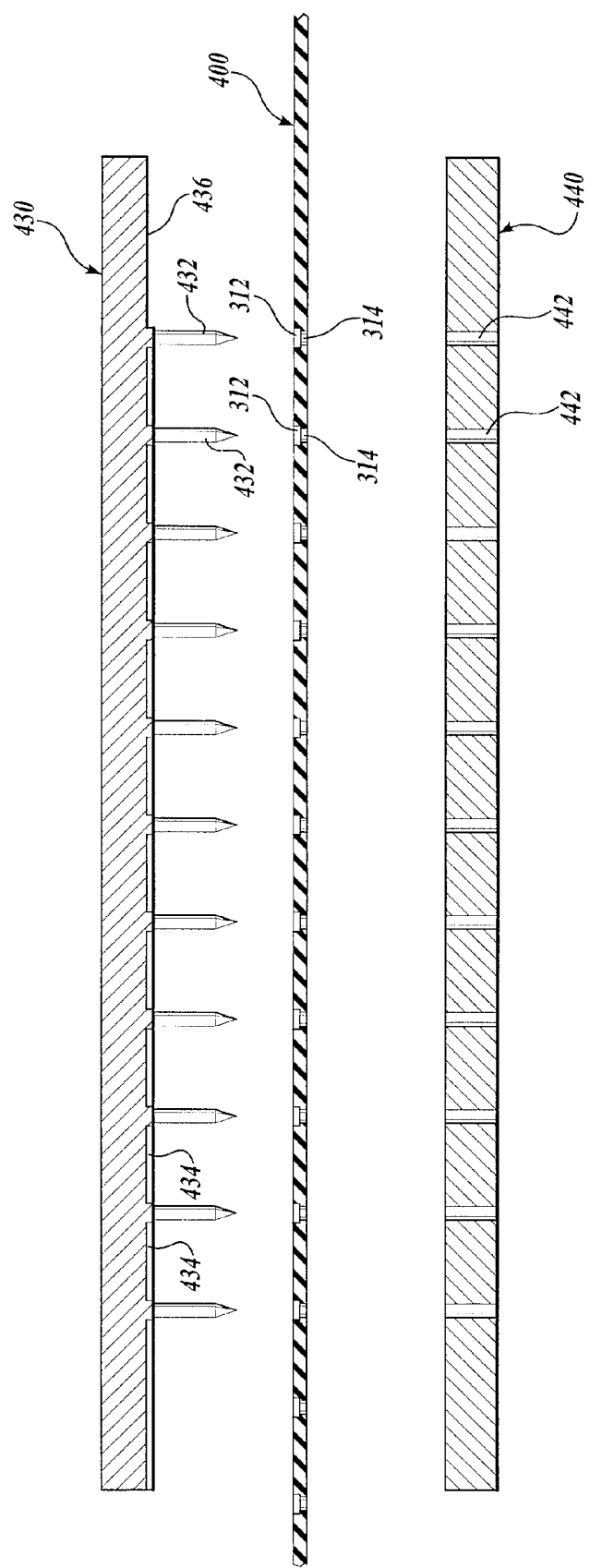
FIG. 17 is a cross-sectional side view of the opposed plates shown in FIG. 16.

FIGS. 16 and 17 show a slightly different configuration of plates 430, 440, similar to the plates of the preceding embodiment, wherein an upper plate 430 includes a plurality of pins 432 that extends downwardly from a lower surface 436 of the upper plate 430. A plurality of elongate protrusions 434 also extends from the lower surface 436. A lower plate 440 includes a plurality of apertures 442 that are sized and shaped to slidably receive the pins 432 in the upper plate 430 when the upper and lower plates are properly aligned. Other than the location of the pins 432 on the upper plate 430 rather than the lower plate 440, this second embodiment is substantially the same as the embodiment disclosed in FIGS. 14 and 15. In particular, the preferred dimensions and operating parameters are the same as those disclosed above.

Figure 18:
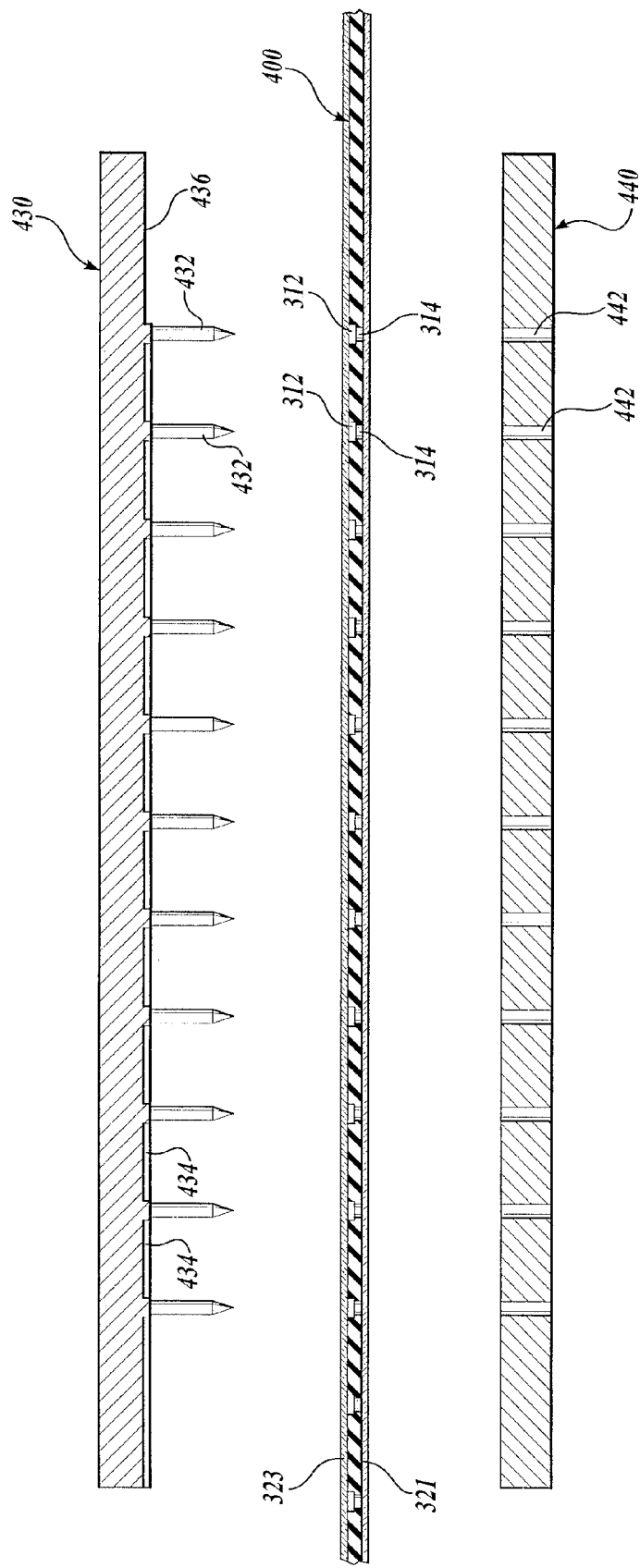
FIG. 18 is a cross-sectional side view similar to FIG. 17, wherein the elastic layer has an upper fabric layer and a lower fabric layer attached thereto prior to forming the channels and apertures.

It is contemplated that any of the elastic layers 310, 320, 330, 340, 350 may have porous outer fabric layers affixed thereto, as discussed above (see FIG. 3), wherein one or both of the outer fabric layers may be applied before, or after, the material is impressed with apertures and channels. For example, as shown in FIG. 18, the sheet 400 may include an upper porous fabric layer 323 attached to an tipper surface and a lower porous fabric layer 321 attached to a lower surface of the inner layer. The fabric layers 321, 323 are preferably a knitted, flexible, and stretchable cloth fabric material that is porous to air and water because of the pores inherently formed by the knitted fabric.

In one method, as shown in FIG. 18, both the upper fabric layer 323 and the lower fabric layer 321 are attached to the elastic layer 310 prior to forming the apertures 314 and channels 312. If the upper fabric layer 323 has sufficient flexibility, it may conform to the channels 312 that are formed in the elastic layer 310, such that the impressed pattern of channels 312 will be apparent in the upper fabric layer 323. It will be appreciated that the resulting material will retain the advantages of having apertures 314 and channels 312 that enhance the heat and vapor transport through the material.

In an alternative method, only the lower fabric layer 321 is applied to the sheet 400 prior to forming the apertures 314 and channels 312, so that when the upper fabric layer 323 is affixed, the channels 312 are already formed in the elastic layer 310 such that the upper fabric layer 323 generally hides the pattern of channels 312. Again, the beneficial aspects of apertures 314 and channels 312 for enhancing heat and vapor transport are retained.

Although the elastic layers disclosed above are suitable for use in a compression brace material, it is contemplated that the materials may also alternatively find many other useful applications—for example, as breathable, insulating layer in sporting outerwear and/or as a component of other clothing such as jackets, gloves, vests, boots and the like.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of manufacturing a material suitable for use in a compression brace material, the method comprising the following steps:
   providing a sheet of closed cell foam material between a first plate having a plurality of spaced-apart pins extending from a first surface, and a second plate having a plurality of spaced-apart apertures, wherein the apertures are sized and spaced to slidably engage the pins when the first plate and second plate are suitably aligned, and further wherein at least one of the first plate and the second plate further includes a plurality of protrusions that are shaped and oriented to produce a pattern of channels on a face of the closed cell foam material;
   heating at least one of the first plate and the second plate to a selected temperature;
   urging the first plate and the second plate together such that the pins on the first plate penetrate the sheet of closed cell foam material and slidably engage the apertures on the second plate;
   maintaining a pressure between the first plate and the second plate for a period of time such that the protrusions impress a plurality of depressions on the sheet of closed cell foam material; and
   separating the first plate from the second plate and removing the closed cell foam material;
   wherein the removed sheet of closed cell foam material comprises a flexible and foldable elastic panel.

2. The method of claim 1, wherein the sheet of closed cell foam material is neoprene, having a thickness between about 2.0 mm and about 10.0 mm.

3. The method of claim 2, wherein at least one of the first plate and the second plate is heated to a temperature between 145° C. and 160° C.

4. The method of claim 3, wherein the pins have a diameter of between 0.5 mm and 3.0 mm.

5. The method of claim 3, wherein the pressure maintained between the first plate and the second plate is about 50 kg/cm$^2$.

6. The method of claim 3, wherein the pressure between the first plate and the second plate is maintained for between about 4 minutes and about 6 minutes.

7. The method of claim 3, wherein the plurality of protrusions are between about 1.0 mm and 2.0 mm high.

8. The method of claim 7, wherein the protrusions consist of a plurality of elongate parallel protrusions having a spacing of between about 10.0 mm and 15.0 mm.

9. The method of claim 7, wherein the plurality of protrusions on the at least one of the first plate and the second plate are shaped to form a plurality of circular features in the sheet of closed cell foam material.

10. A method of manufacturing a perforated orthopedic compression brace panel comprising the following steps:
   providing a first plate having a plurality of spaced-apart pins extending from a first surface, and a second plate having a plurality of similarly spaced-apart apertures and wherein at least one of the first plate and the second plate further includes a plurality of protrusions;
   heating at least one of the first plate and the second plate to a selected temperature;
   inserting an closed-cell foam elastic panel between the first plate and the second plate, and wherein the plurality of protrusions are shaped and oriented to produce a pattern of depressions on a face of the closed-cell foam elastic panel;
   urging one of the first and second plate towards the other of the first and second plate such that the pins on the first plate penetrate the elastic panel and slidably engage the apertures on the second plate;
   maintaining a pressure between the first plate and the second plate for a period of time such that the protrusions form corresponding depressions in the elastic panel; and
   separating the first plate from the second plate and removing the elastic panel;
   wherein the removed elastic panel comprises a flexible and foldable elastic panel.

11. The method of claim 10, wherein the elastic panel comprises a sheet of neoprene, having a thickness between about 2.0 mm and about 10.0 mm.

12. The method of claim 10, wherein selected temperature that the at least one of the first plate and the second plate is heated to is between 145° C. and 160° C.

13. The method of claim 10, wherein the pins have a diameter of between 0.5 mm and 3.0 mm.

14. The method of claim 10, wherein the pressure maintained between the first plate and the second plate is about 50 kg/cm$^2$.

15. The method of claim 10, wherein the pressure between the first plate and the second plate is maintained for between about 4 minutes and about 6 minutes.

16. The method of claim 10, wherein the plurality of protrusions are between about 1.0 mm and 2.0 mm high.

17. The method of claim 10, wherein the plurality of protrusions consist of a plurality of elongate parallel protrusions having a spacing of between about 10.0 mm and 15.0 mm.

18. The method of claim 10, wherein the plurality of protrusions on the at least one of the first plate and the second plate are shaped to form a plurality of circular features in the sheet of closed cell foam material.

* * * * *